United States Patent
Wei

(10) Patent No.: US 8,084,223 B2
(45) Date of Patent: Dec. 27, 2011

(54) DETECTION OF FALSE RESULTS IN ASSAYS

(75) Inventor: Tie Quan Wei, Wilmington, DE (US)

(73) Assignee: Siemens Healthcare Diagnostics Inc., Deerfield, IL (US)

( * ) Notice: Subject to any disclaimer, the term of this patent is extended or adjusted under 35 U.S.C. 154(b) by 304 days.

(21) Appl. No.: 12/409,302

(22) Filed: Mar. 23, 2009

(65) Prior Publication Data

US 2010/0240073 A1    Sep. 23, 2010

(51) Int. Cl.
*G01N 33/00* (2006.01)
*G01N 33/86* (2006.01)

(52) U.S. Cl. ....... 435/7.25; 435/7.1; 435/7.93; 436/520; 436/522; 436/523; 436/526; 436/16; 436/17; 436/70; 436/175; 436/177; 424/9.2

(58) Field of Classification Search .................... 435/7.1, 435/7.2, 7.25, 7.93; 436/520, 16, 17, 70, 436/175, 177, 522, 523, 526; 424/9.2
See application file for complete search history.

(56) References Cited

U.S. PATENT DOCUMENTS

| | | |
|---|---|---|
| 5,447,870 A | 9/1995 | Lau |
| 5,593,638 A | 1/1997 | Davis |
| 6,087,088 A | 7/2000 | Piran et al. |
| 6,268,167 B1 | 7/2001 | Wild et al. |
| 6,528,321 B1 | 3/2003 | Fitzgerald et al. |
| 7,186,518 B2 | 3/2007 | Wang et al. |
| 2007/0224651 A1 | 9/2007 | Zhang et al. |
| 2007/0238653 A1 | 10/2007 | Owens et al. |
| 2007/0292891 A1 | 12/2007 | Wei et al. |
| 2008/0195062 A1 | 8/2008 | Caprioli |

OTHER PUBLICATIONS

Owens et al. Correction of Factitious Hyperkalemia in hemolyzed Specimens, The American Journal of Emergency Medicine, Nov. 2005; vol. 23, No. 7; pp. 872-875).*

Bouzas et al. Effect of the hematocrit and its correction on the relationship between blood tacrolimus concentrations obtained using the microparticle enzyme immunoassay (MEIA) and enzyme multiplied immunoassay technique (EMIT). Clinical laboratory, (2007) vol. 53, No. 9-12, pp. 591-596.*

Owens et al., Correction of Factitious Hyperkalemia in hemolyzed Specimens, The American Journal of Emergency Medicine, Nov. 2005; vol. 23, No. 7; pp. 872-875; especially, Abstract, Methods, Results and Conclusions.

* cited by examiner

*Primary Examiner* — Gail R Gabel
(74) *Attorney, Agent, or Firm* — Theodore J. Leitereg

(57) ABSTRACT

Methods and reagents are disclosed for detecting a false result in an assay for determining a concentration of an analyte in a whole blood sample suspected of containing the analyte. The method comprises determining by means of the assay a concentration of the analyte utilizing a hemolyzed portion of the blood sample to obtain concentration value 1 and determining by means of the assay a concentration of the analyte utilizing a non-hemolyzed portion of the blood sample and multiplying the concentration times a hematocrit factor to obtain concentration value 2. A ratio of concentration value 1 divided by concentration value 2 is determined and is compared to a predetermined ratio of known reliability. If the ratio is less than the predetermined ratio, a false result is indicated.

20 Claims, No Drawings

DETECTION OF FALSE RESULTS IN ASSAYS

BACKGROUND

The invention relates to compounds, methods and kits for the determination of the concentration of an analyte in a blood sample.

The body relies upon a complex immune response system to distinguish self from non-self. At times, the body's immune system must be controlled in order to either augment a deficient response or suppress an excessive response. For example, when organs such as kidney, heart, heart-lung, bone marrow and liver are transplanted in humans, the body will often reject the transplanted tissue by a process referred to as allograft rejection.

In treating allograft rejection, the immune system is frequently suppressed in a controlled manner with drug therapy. Immunosuppressant drugs are carefully administered to transplant recipients in order to help prevent allograft rejection of non-self tissue. Two most commonly administered immunosuppressive drugs to prevent organ rejection in transplant patients are Cyclosporine (CSA) and FK-506 (FK or tacrolimus). Another drug that finds use as an immunosuppressant in the United States and other countries is sirolimus, also known as rapamycin. Derivatives of sirolimus are also said to be useful as immunosuppressants. Such derivatives include, for example, Everolimus, and the like.

The side effects associated with some immunosuppressant drugs can be controlled in part by carefully controlling the level of the drug present in a patient. Therapeutic monitoring of concentrations of immunosuppressant drugs and related drugs in blood is required to optimize dosing regimes to ensure maximal immunosuppression with minimal toxicity. Although immunosuppressant drugs are highly effective immunosuppressive agents, their use must be carefully managed because the effective dose range is often narrow and excessive dosage can result in serious side effects. On the other hand, too little dosage of an immunosuppressant can lead to tissue rejection. Because the distribution and metabolism of an immunosuppressant drug can vary greatly between patients and because of the wide range and severity of adverse reactions, accurate monitoring of the drug level is essential.

In therapeutic drug monitoring field, selectively detecting the parent drug over its metabolites is often an important goal for designing immunoassays. This is especially true for immunosuppressant drugs. For that reason, HPLC tandem MS assays have become standard methods for the measurement of sirolimus and other immunosuppressant drugs due to their ability to selectively measure the parent drug. However, the above methods are costly and time-consuming and are often employed to verify positive results obtained by another assay method rather than used in laboratories as an initial determination.

Most whole blood assays for immunosuppressant drugs require a manual step using reagents to extract the drug from blood constituents. As a result, the drug molecules and drug metabolite molecules are dissociated from endogenous binding proteins and are extracted into a relatively clean solution in which plasma proteins and lipoprotein particles as well as most other molecules are removed. Because precipitation techniques are usually used, the extracted sample is basically free of most blood macromolecules including drug-binding proteins. Thus, in the extracted samples, the parent drug and its metabolites are dissolved as unbound, individual molecules and compete with one another for reaction with an assay antibody in the immunoreaction mixture. The binding of assay antibody to the drug occurs in the absence of most endogenous substances in these assays. The cross-reactivity of a drug metabolite depends mostly on its antibody binding affinity in such assays.

In a homogeneous assay for an immunosuppressant drug where there is no manual extraction or separation of the drug from blood constituents, an antibody for the immunosuppressant drug has to detect the drug in the presence of most or all blood constituents, the presence of which might interfere with the binding of the antibody to the immunosuppressant drug. Furthermore, the samples contain metabolites of the drug and high metabolite cross-reactivity presents a serious accuracy issue in assays for immunosuppressant drugs.

There is, therefore, a continuing need to develop fast and accurate diagnostic methods to measure levels of immunosuppressant drugs or derivatives thereof in patients. The methods should be fully automated and be accurate even when conducted on whole blood samples with no-extraction using a homogeneous assay where an antibody employed in the assay has to detect the drug in the presence of most, if not all, blood constituents and in the presence of drug metabolites. The assay should selectively detect the parent drug while minimizing inaccuracies resulting from the cross-reactivity of its metabolites. The detection of false results is important to the accuracy of the methods.

SUMMARY

One embodiment of the present invention is a method for detecting a false result in an assay for determining a concentration of an analyte in a whole blood sample suspected of containing the analyte. The method comprises determining by means of the assay a concentration of the analyte utilizing a hemolyzed portion of the blood sample to obtain concentration value 1 and determining by means of the assay a concentration of the analyte utilizing a non-hemolyzed portion of the blood sample and multiplying the concentration times a hematocrit factor to obtain concentration value 2. A ratio of concentration value 1 divided by concentration value 2 is determined and is compared to a predetermined ratio of known reliability. If the ratio is less than the predetermined ratio, a false result is indicated.

Another embodiment of the present invention is a method for detecting a false result in an assay for determining a concentration of an analyte in a whole blood sample suspected of containing the analyte. Concentration value 1 is obtained by determining, by means of the assay, a concentration of the analyte utilizing a hemolyzed portion of the blood sample. Concentration value 2 is obtained by determining, by means of the assay, a concentration of the analyte utilizing a non-hemolyzed portion of the blood sample and multiplying the concentration times a hematocrit factor. The hematocrit factor is the following equation: $1/(1-\text{hematocrit \% in decimal form})$. The assay comprises (i) adding to a medium, which comprises the blood sample of the determination of concentration values 1 or 2 above, reagents for determining the concentration of the analyte in the blood sample wherein the reagents comprise at least one antibody for the analyte, and (ii) measuring an amount of a complex comprising the analyte and the antibody for the analyte and relating the amount of the complex to the concentration of the analyte in the blood sample. A ratio of concentration value 1 divided by concentration value 2 is determined and is compared to a predetermined ratio of known reliability. If the ratio is less than the predetermined ratio, a false result is indicated. The predetermined ratio is a ratio of a concentration of the analyte in a hemolyzed portion of a whole blood sample that contains the analyte divided by a concentration of analyte in a plasma portion of the whole blood sample. The predetermined ratio of known reliability is determined by a method that is independent of factors that produce a false result in the assay.

DETAILED DESCRIPTION OF SPECIFIC EMBODIMENTS

General Discussion

The present invention is directed to the accurate measurement of drug concentration in whole blood samples by determining whether an assay result is false. The present inventors, recognizing that a majority of immunosuppressant drugs such as, for example, cyclosporin A and tacrolimus, are found in erythrocytes, developed a method for detecting false results wherein, if the method detects elevated and similar drug concentrations in matched non-hemolyzed (mimic the plasma drug concentration times a hematocrit factor) and hemolyzed whole blood (the total drug concentration in blood) samples from the same whole blood sample, the results of the assay are false. If drug concentrations in matched hemolyzed and non-hemolyzed blood samples are close and both are significantly elevated, the assay signal may be attributed to the presence of interfering substances such as endogenous antibodies found in plasma. In such a situation, the drug concentration measured in hemolyzed whole blood should not be reported. Furthermore, if drug concentration in non-hemolyzed whole blood is measured higher than that in hemolyzed whole blood (a situation that may arise because the space available for immunobinding is smaller in non-hemolyzed samples; hence, higher binding may result, which means higher false signal), and the drug concentration in both hemolyzed and non-hemolyzed whole blood are elevated, the assay signal must be generated by interfering substances such as endogenous interfering antibodies. The false results may be flagged so that they do not interfere with an accurate determination of drug concentration.

Embodiments of the present methods comprise (a) determining by means of the assay a concentration of the analyte utilizing a hemolyzed portion of the blood sample to obtain concentration value 1, (b) determining by means of the assay a concentration of the analyte utilizing a non-hemolyzed portion of the blood sample and multiplying the concentration times a hematocrit factor to obtain concentration value 2, (c) determining a ratio of concentration value 1 divided by concentration value 2 and (d) comparing the ratio to a predetermined ratio of known reliability. If the ratio is less than the predetermined ratio, a false result is indicated.

Some embodiments of the present methods are applicable to homogeneous immunoassays, which may also be referred to as essentially partition-free immunoassays. The present methods have application to fully automated homogeneous assays in which, prior to the assay, there is no extraction or separation of the analyte from other constituents of the sample including analyte metabolites. In a "non-manual extraction" assay, a sample such as a whole blood sample, without extraction in an organic solvent, is combined with reagents for conducting an assay for the analyte in a suitable medium and the assay method is conducted. In accordance with present embodiments the assay method is conducted on a portion of the whole blood sample that is hemolyzed and on a portion of the whole blood sample that is not hemolyzed. For the hemolyzed blood sample, the sample is first combined in a suitable medium with a hemolyzing agent and the medium is incubated to allow for hemolysis and release of the drug from erythrocytes and other blood constituents. Following the incubation period, reagents for conducting the assay are added. For the non-hemolyzed blood sample, the reagents for conducting the assay are combined with the blood sample in a suitable medium and the assay is conducted; no hemolyzing agent is involved.

The present embodiments have particular application to the measurement of erythrocytophilic drugs. The term "erythrocytophilic drug" as used herein refers to a drug, usually a therapeutic drug, where the drug exhibits a characteristic of absorption by an erythrocyte. The erythrocytophilic drug is usually hydrophobic and exhibits a characteristic of absorption by a lipophilic moiety such as, for example, a lipoprotein, e.g., an erythrocyte, or a drug-specific binding protein, or of reduced solubility in a polar medium. The absorption of the drug by an erythrocyte is at least about 70%, or at least about 75%, or at least about 80%, or at least about 85%, or at least about 90%, or at least about 95%, or at least about 96%, or at least about 97%, or at least about 98%, or at least about 99%, for example.

Immunosuppressant drugs are an example of erythrocytophilic drugs and are also considered as hydrophobic drugs. Immunosuppressant drugs are therapeutic drugs that are administered to transplant recipients in order to help prevent allograft rejection of non-self tissue. Immunosuppressive drugs can be classified as follows: glucocorticoids, cytostatics, antibodies, drugs acting on immunophilins, and other drugs such as interferons, opiates INF binding proteins, mycophenolate, FTY720 and the like. A particular class of immunosuppressant drugs comprises those drugs that act on immunophilins. Immunophilins are an example of high-affinity, specific binding proteins having physiological significance. Two distinct families of immunophilins are presently known: cyclophilins and macrophilins, the latter of which specifically bind, for example, tacrolimus or sirolimus. The immunosuppressant drugs that act on immunophilin include, for example, cyclosporin (including cyclosporin A, cyclosporin B, cyclosporin C, cyclosporin D, cyclosporin E, cyclosporin F, cyclosporin G, cyclosporin H, cyclosporin I), tacrolimus (FK506, PROGRAF®), sirolimus (rapamycin, RAPAMUNE®), everolimus (RAD, CERTICAN®) and so forth.

The phrase "at least" as used herein means that the number of specified items may be equal to or greater than the number recited. The phrase "about" as used herein means that the number recited may differ by plus or minus 10%; for example, "about 5" means a range of 4.5 to 5.5.

The sample to be analyzed is one that is suspected of containing one or more erythrocytophilic drug analytes. The sample typically comprises one or more endogenous binding moieties that bind to the erythrocytophilic drug. The endogenous binding moieties may be binding proteins that bind a hydrophobic drug such as a lipoprotein, e.g., a protein that comprises a hydrophobic cavity on the surface or other spatial features that bind the hydrophobic drug such as cholesterol, triglyceride, and so forth. The sample is whole blood, which is unfractionated blood or blood that comprises both red cells and plasma. The samples are preferably from humans or animals. The sample is not pretreated to remove such endogenous binding moieties.

The sample can be prepared in any convenient medium that does not interfere with an assay; an aqueous medium generally is employed. The nature of the medium is discussed in more detail below. A releasing agent for the erythrocytophilic drug may be included in the medium, which may also include a hemolytic agent for those sample portions that are to be hemolyzed. The volume of the hemolyzed and non-hemolyzed portions of the whole blood sample that is tested is determined by a number of factors that include, for example, the expected concentration of the erythrocytophilic drug in the sample. The volume of the sample portion is about 1 µL to about 100 µL, or about 2 µL to about 100 µL, or about 5 µL to about 100 µL, or about 10 µL to about 100 µL, or about 1 µL to about 80 µL, or about 1 µL to about 60 µL, or about 1 µL to about 40 µL, or about 1 µL to about 20 µL, or about 5 µL to about 50 µL, or about 10 µL to about 50 µL, for example.

A hemolytic agent is a compound or mixture of compounds that disrupt the integrity of the membranes of red blood cells thereby releasing intracellular contents of the cells and, in particular, erythrocytes. Numerous hemolytic agents are known in the art. Hemolytic agents include, for example, non-ionic detergents, anionic detergents, amphoteric detergents, low ionic strength aqueous solutions (hypotonic solutions), bacterial agents, antibodies that cause complement dependent lysis, and the like. Non-ionic detergents that may be employed as the hemolytic agent include both synthetic detergents and natural detergents. Examples of synthetic detergents include TRITON™ X-100, TRITON™ N-101, TRITON™ X-114, TRITON™ X-405, TRITON™ SP-135, TWEEN® 20 (polyoxyethylene (20) sorbitan monolaurate), TWEEN® 80 (polyoxyethylene (20) sorbitan monooleate), DOWFAX®, ZONYL®, pentaerythrityl palmitate, ADOGEN® 464, ALKANOL® 6112 surfactant, allyl alcohol 1,2-butoxylate-block-ethoxylate HLB 6, BRIJ®, ethylenediamine tetrakis(ethoxylate-block-propoxylate) tetrol, IGEPAL®, MERPOL®, poly(ethylene glycol), 2-[ethyl [(heptadecafluorooctyl)sulfonyl]amino]ethyl ether, polyethylene-block-poly(ethylene glycol), polyoxyethylene sorbitan tetraoleate, polyoxyethylene sorbitol hexaoleate, TERGITOL® NP-9, GAFAC® (RHODAFAC®, an alkyl polyoxyethylene glycol phosphate ester such as, for example, alpha-dodecyl-omega-hydroxypoly(oxy-1,2-ethanediyl) phosphate), and EP110® and the like. Naturally-occurring detergents that may be employed as the hemolytic agent include, for example, saponins, sodium or potassium neutralized fatty acid, neutralized phospholipids, diacylglycerol, neutralized phosphatidyl serine, phosphatidate, neutralized phosphatidyl ethanoliamin, phosphatidyl choline, phosphatidyl inositol, phosphatidylcholine, bile salt, unesterified cholesterol, neutralized sphingosine, ceramide, and the like. Combinations of one or more synthetic detergents or one or more naturally occurring detergents and combinations of synthetic detergents and naturally occurring detergents may also be employed.

The nature and amount or concentration of hemolytic agent employed depends on the nature of the sample, the volume of the sample portion, the nature of the erythrocytophilic drug, the nature of the rest of the reagent components, the reaction conditions, and the like. The amount of the hemolytic agent is at least sufficient to cause lysis of red blood cells to release contents of the cells. In some embodiments the amount of the hemolytic agent is about 0.0001% to about 0.5%, about 0.001% to about 0.4%, about 0.01% to about 0.3%, about 0.01% to about 0.2%, about 0.1% to about 0.3%, about 0.2% to about 0.5%, about 0.1% to about 0.2%, and so forth (percent is weight/volume).

A releasing agent may be employed in some embodiments to displace the erythrocytophilic drug from endogenous binding moieties. The releasing agent can, and does in many instances, displace metabolites of the erythrocytophilic drug from endogenous binding moieties. In many embodiments the releasing agent has high binding affinity to the endogenous binding proteins so that it readily displaces the erythrocytophilic drug, and its metabolites, from endogenous binding proteins. In addition, the releasing agent does not bind to any significant degree to an antibody for the drug that is used in the assay. By the phrase "does not bind to any significant degree" is meant that the extent of binding should be low enough so that an accurate assay for the drug may be carried out. The releasing agent may be any moiety, either a single compound or a mixture of compounds, which accomplishes the desired result of displacement with no significant binding to an assay antibody. In many embodiments the releasing agent displaces the erythrocytophilic drug and its metabolite from endogenous binding substances to render both the erythrocytophilic drug and the metabolites substantially equally accessible to an antibody for the erythrocytophilic drug. "Substantially equally accessible" means that the amount of erythrocytophilic drug available for binding to antibody does not vary to any significant extent from the total amount of metabolites of the erythrocytophilic drug that are available for binding to the antibody. The amount of metabolites available for binding to an antibody for the erythrocytophilic drug is dependent on considerations such as, for example, the binding affinity of particular metabolites for the antibody for the erythrocytophilic drug. The above percentages are based on the assumption that the drug metabolites have approximately the same binding affinity for the antibody for the erythrocytophilic drug as the erythrocytophilic drug itself. Otherwise, the above percentages should be adjusted based on the actual binding affinity of the erythrocytophilic drug metabolites.

In some embodiments the releasing agent is an analog, including structural analogs, of the erythrocytophilic drug. An erythrocytophilic drug analog is a modified drug that can displace the analogous erythrocytophilic drug from a binding protein but does not compete to any substantial degree for a receptor such as an antibody for the erythrocytophilic drug. The modification provides means to join an erythrocytophilic drug analog to another molecule. The erythrocytophilic drug analog will usually differ from the erythrocytophilic drug by more than replacement of a hydrogen with a bond which links the drug analog to a hub or label, but need not. The erythrocytophilic drug analog may be, for example, the erythrocytophilic drug conjugated to another molecule through a linking group, and so forth. For erythrocytophilic drugs that comprise a hydroxy or carboxylic acid functionality, the releasing agent may be an ester of the erythrocytophilic drug, which has a high binding affinity for endogenous binding proteins relative to the erythrocytophilic drug to be detected and which has no significant binding affinity for an antibody for the erythrocytophilic drug. For example, in a determination for sirolimus, an ester of sirolimus may be employed as the releasing agent so long as it meets the above requirements. A structural analog is a moiety that has the same or similar structural or spatial characteristics as the erythrocytophilic drug such that the structural analog accomplishes the same or similar result as the analog of the erythrocytophilic drug. The structural analog may be, for example, another compound that is related to the erythrocytophilic drug. For example, in a determination for sirolimus, an ester of tacrolimus may be employed as the releasing agent. The ester may be, for example, a carbamate, a carbonate, an ester of a $C_1$ to $C_6$ carboxylic acid, and the like. See, for example, U.S. Pat. No. 7,186,518, the relevant disclosure of which is incorporated herein by reference. Other examples of releasing agents include [$Thr_2$, $Leu_5$, $D-Hiv_8$, $Leu_{10}$]-cyclosporin A for cyclosporin A, FK506 for sirolimus, sirolimus for FK506, and the like. See, for example, U.S. Pat. No. 6,187,547, the relevant disclosure of which is incorporated herein by reference.

The concentration of the releasing agent in the medium is that sufficient to achieve the desired result of displacing the erythrocytophilic drug, and in many instances the metabolites of the erythrocytophilic drug, from endogenous binding moieties to render the drug and metabolites accessible for binding to an antibody for the drug as discussed above. The amount or concentration of the releasing agent employed depends on the nature of the sample, the nature of the erythrocytophilic drug, the nature of the drug metabolites, the nature of other reagent components, the reaction conditions and the like. In some embodiments the amount of the releasing agent is about 0.000001% to about 0.5%, about 0.0001% to about 0.4%, about 0.001% to about 0.3%, about 0.01% to about 0.2%, about 0.1% to about 0.3%, about 0.2% to about 0.5%, about 0.1% to about 0.2%, and so forth (percent is weight/volume). Other reagents may be employed such as, for example solubility reagents, a small amount of an organic solvent such as, for example, methanol, ethanol, isopropanol, methoxy propanol and DMSO.

Preparation of Sample Portions

As mentioned above, embodiments of the present methods involve (a) determining, by means of an assay, a concentration of the analyte utilizing a hemolyzed portion of the blood sample to obtain concentration value 1, (b) determining, by means of the assay, a concentration of the analyte utilizing a non-hemolyzed portion of the blood sample and multiplying the concentration times a hematocrit factor to obtain concentration value 2. Accordingly, a portion of a whole blood sample is treated first with a hemolyzing agent to prepare a hemolyzed portion. In some embodiments the sample, a hemolytic agent and a releasing agent (if employed) are combined in a medium, which, as mentioned above, is usually an aqueous medium and is referred to herein as a hemolyzing medium. All of the above may be combined simultaneously in the medium or one or more of the above reagents may be added sequentially in concentrations as discussed above. The medium may also comprise one or more preservatives as are known in the art such as, for example, sodium azide, neomycin sulfate, PROCLIN® 300, Streptomycin, and the like. The pH for the medium will usually be in the range of about 4 to about 11, more usually in the range of about 5 to about 10, and preferably in the range of about 6.5 to about 9.5.

Various buffers may be used to achieve the desired pH and maintain the pH during the incubation period. Illustrative buffers include borate, phosphate, carbonate, tris, barbital, PIPES, HEPES, MES, ACES, MOPS, BICINE, and the like. The medium may also comprise agents for preventing the formation of blood clots. Such agents are well known in the art and include, for example, EDTA, EGTA, citrate, heparin, and the like. Various ancillary materials may be employed in the above methods. For example, in addition to buffers and preservatives, the medium may comprise stabilizers for the medium and for the reagents employed. All of the above materials are present in a concentration or amount sufficient to achieve the desired effect or function.

The medium is incubated under conditions for hemolyzing cells in the sample and for releasing the hydrophobic drug and its metabolites from endogenous binding moieties (in embodiments where a releasing agent is employed). The incubation period may be about 1 second to about 60 minutes, or about 1 second to about 6 minutes, or about 1 second to about 5 minutes, or about 1 second to about 3 minutes, or about 1 second to about 2 minutes, or about 1 second to about 1 minute, or about 1 second to about 30 seconds, or about 1 second to about 20 seconds, or about 1 second to about 10 seconds, or about 5 seconds to about 60 minutes, or about 5 seconds to about 6 minutes, or about 5 seconds to about 5 minutes, or about 5 seconds to about 3 minutes, or about 5 seconds to about 2 minutes, or about 5 seconds to about 1 minute, or about 5 seconds to about 30 seconds, or about 5 seconds to about 20 seconds, or about 5 seconds to about 10 seconds, or about 10 seconds to about 60 minutes, or about 10 seconds to about 6 minutes, or about 10 seconds to about 5 minutes, or about 10 seconds to about 3 minutes, or about 10 seconds to about 2 minutes, or about 10 seconds to about 1 minute, or about 10 seconds to about 30 seconds, or about 10 seconds to about 20 seconds, or about 20 seconds to about 60 minutes, or about 20 seconds to about 6 minutes, or about 20 seconds to about 5 minutes, or about 20 seconds to about 3 minutes, or about 20 seconds to about 2 minutes, or about 20 seconds to about 1 minute, or about 20 seconds to about 30 seconds, or about 30 seconds to about 60 minutes, or about 30 seconds to about 6 minutes, or about 30 seconds to about 5 minutes, or about 30 seconds to about 3 minutes, or about 30 seconds to about 2 minutes, or about 30 seconds to about 1 minute, or about 1 minute to about 30 minutes, or about 1 minute to about 20 minutes, or about 1 minute to about 10 minutes, for example.

The temperature during the incubation is usually about 10° C. to about 45° C., or about 10° C. to about 35° C., or about 10° C. to about 25° C., or about 15° C. to about 45° C., or about 15° C. to about 35° C., or about 15° C. to about 25° C., or about 20° C. to about about 20° C. to about 35° C., or about 20° C. to about 25° C., for example.

In accordance with the present embodiments, another portion of the whole blood sample is the non-hemolyzed portion and is not treated with hemolyzing agent. However, if the hemolyzed portion is treated with a releasing agent, then the non-hemolyzed portion is also treated with a releasing agent. In the latter case, a portion of a whole blood sample is treated first with a releasing agent. The sample and a releasing agent (if employed) are combined in a medium, which, as mentioned above, is usually an aqueous medium. The reagents may be combined simultaneously in the medium or one or more of the above reagents may be added sequentially in concentrations as discussed above. The medium may also comprise one or more preservatives as are known in the art. The pH of the medium, the duration of the treatment, the temperature and so forth are as discussed above for the hemolyzing and releasing step on the hemolyzed portion of the blood sample.

General Description of Assays for an Erythrocytophilic Drug

Following the preparation of the hemolyzed portion and the non-hemolyzed portion of the whole blood sample, the concentration of analyte is determined for each portion. Any suitable assay may be employed for determining the concentration of analyte in the hemolyzed and non-hemolyzed portions. The assays may be conducted on the portions as an immediate continuation of the pretreatment of the portions or the assay may be carried out at a point thereafter. The assays are conducted by combining the respective hemolyzed and non-hemolyzed portions of the whole blood sample with reagents for determining the presence and/or amount of the erythrocytophilic drug in the sample are added to the medium. The nature of the reagents is dependent on the particular type of assay to be performed. In general, the assay is a method for the determination or measuring of the presence and/or amount of an erythrocytophilic analyte. Various assay methods are discussed below by way of illustration and not limitation.

In many embodiments the reagents comprise at least one antibody for the erythrocytophilic drug. By the phrase "antibody for the erythrocytophilic drug" is meant an antibody that binds specifically to the erythrocytophilic drug and does not bind to any significant degree to other substances that would distort the analysis for the erythrocytophilic drug.

Antibodies specific for an erythrocytophilic drug for use in immunoassays can be monoclonal or polyclonal. Such antibodies can be prepared by techniques that are well known in the art such as immunization of a host and collection of sera (polyclonal) or by preparing continuous hybrid cell lines and collecting the secreted protein (monoclonal) or by cloning and expressing nucleotide sequences or mutagenized versions thereof coding at least for the amino acid sequences required for specific binding of natural antibodies.

Antibodies may include a complete immunoglobulin or fragment thereof, which immunoglobulins include the various classes and isotypes, such as IgA, IgD, IgE, IgG1, IgG2a, IgG2b and IgG3, IgM, etc. Fragments thereof may include Fab, Fv and F(ab')$_2$, Fab', and the like. In addition, aggregates, polymers, and conjugates of immunoglobulins or their fragments can be used where appropriate so long as binding affinity for a particular molecule is maintained.

As discussed above, an antibody selected for use in an immunoassay for an erythrocytophilic drug, for example, should specifically and preferentially bind the erythrocytophilic drug and its pharmaceutically active metabolites over other ligands such as other metabolites or related drugs. For example, an antibody for tacrolimus should specifically and preferentially bind tacrolimus over, e.g., rapamycin. In general, an antibody should be capable of distinguishing between one erythrocytophilic drug relative to a second erythrocytophilic drug. At least about 5-fold, at least about 10-fold, or at least about 20-fold, of the first erythrocytophilic drug will be bound to the antibody if the antibody is combined with a sample containing the erythrocytophilic drug. While the binding also depends on relative concentration of the erythrocytophilic drug, the binding will be higher for the first erythrocytophilic drug if the binding constant for the first erythrocytophilic drug is greater than the binding constant for the second erythrocytophilic drug, at least about 10-fold higher or at least about 50-fold higher and up to 1000-fold or higher.

Other reagents are included in the assay medium depending on the nature of the assay to be conducted. Such assays usually involve reactions between binding partners such as an erythrocytophilic drug analyte and a corresponding antibody or the binding between an antibody and a corresponding binding partner such as a second antibody that binds to the first antibody. Accordingly, the binding partner may be a protein, which may be an antibody or an antigen. The binding partner may be a member of a specific binding pair ("sbp member"), which is one of two different molecules, having an area on the surface or in a cavity, which specifically binds to and is thereby defined as complementary with a particular spatial and polar organization of the other molecule. The members of the specific binding pair will usually be members of an immunological pair such as antigen-antibody, although other specific binding pairs such as biotin-avidin, hormones-hormone receptors, enzyme-substrate, nucleic acid duplexes, IgG-protein A, polynucleotide pairs such as DNA-DNA, DNA-RNA, and the like are not immunological pairs but are included within the scope of sbp member.

Accordingly, specific binding involves the specific recognition of one of two different molecules for the other compared to substantially less recognition of other molecules. On the other hand, non-specific binding involves non-covalent binding between molecules that is relatively independent of specific surface structures. Non-specific binding may result from several factors including hydrophobic interactions between molecules. In many embodiments of assays, preferred binding partners are antibodies and the assays are referred to as immunoassays.

Many types of immunoassays may be employed in the present methods to determine the presence and/or amount of an erythrocytophilic drug analyte in a sample suspected of containing such analytes. The immunoassays may involve labeled or non-labeled reagents. Immunoassays involving non-labeled reagents usually comprise the formation of relatively large complexes involving one or more antibodies. Such assays include, for example, immunoprecipitin and agglutination methods and corresponding light scattering techniques such as, e.g., nephelometry and turbidimetry, for the detection of antibody complexes. Labeled immunoassays include enzyme immunoassays, fluorescence polarization immunoassays, radioimmunoassay, inhibition assay, induced luminescence, fluorescent oxygen channeling assay, and so forth.

Examination Step

In a next step of the assay, the medium is examined for the presence of a complex comprising the erythrocytophilic drug and the antibody for the erythrocytophilic drug. The presence and/or amount of the complex indicate the presence and/or amount of the erythrocytophilic drug in the sample if the result is an accurate result and not a false result.

The phrase "measuring the amount of an erythrocytophilic drug analyte" refers to the quantitative, semi quantitative and qualitative determination of the erythrocytophilic drug analyte. Methods that are quantitative, semiquantitative and qualitative, as well as all other methods for determining the erythrocytophilic drug analyte, are considered to be methods of measuring the amount of the erythrocytophilic drug analyte. For example, a method, which merely detects the presence or absence of the erythrocytophilic drug analyte in a sample suspected of containing the erythrocytophilic drug analyte, is considered to be included within the scope of the present invention. The terms "detecting" and "determining," as well as other common synonyms for measuring, are contemplated within the scope of the present invention.

In many embodiments the examination of the medium involves detection of a signal from the medium. The presence and/or amount of the signal are related to the presence and/or amount of the erythrocytophilic drug in the sample if the assay is accurately determining such drug. The particular mode of detection depends on the nature of the sps. As discussed above, there are numerous methods by which a label of an sps can produce a signal detectable by external means, desirably by visual examination, and include, for example, electromagnetic radiation, electrochemistry, heat, radioactivity detection, chemical reagents and so forth.

Activation of a signal producing system depends on the nature of the signal producing system members. For those members of a signal producing system that are activated with light, the member is irradiated with light. For members of signal producing systems that are on the surface of a particle, addition of a base may result in activation. Other activation methods will be suggested to those skilled in the art in view of the disclosures herein. For some signal producing systems, no agent for activation is necessary such as those systems that involve a label that is a radioactive label, an enzyme, and so forth. For enzyme systems, addition of a substrate and/or a cofactor may be necessary.

The examination for presence and/or amount of the signal also includes the detection of the signal, which is generally merely a step in which the signal is read. The signal is normally read using an instrument, the nature of which depends on the nature of the signal. The instrument may be a spectrophotometer, fluorometer, absorption spectrometer, luminometer, chemiluminometer, actinometer, photographic instrument, and the like. The presence and amount of signal detected is related to the presence and amount of the hydrophobic drug compound present in a sample if the assay is making an accurate determination. Temperatures during measurements generally range from about 10° to about 70° C., or from about 20° to about 45° C., or about 20° to about 25° C., for example approach standard curves are formed using known concentrations of the analytes to be screened. As discussed herein, calibrators and other controls may also be used.

Comparison of Assay Results to Determine False Results

As mentioned earlier, the present embodiments allow for detection of false results in the above assay determinations. In the present embodiments an assay is conducted on a hemolyzed portion of a blood sample to determine a concentration of the analyte, which may be designated as concentration value 1. The same assay is employed to determine a concentration of the analyte in a non-hemolyzed portion of the blood sample; this concentration is multiplied by a hematocrit factor to obtain concentration value 2. Multiplication of the concentration obtained for the non-hemolyzed sample by the hematocrit factor produces a value that closely approximates the concentration that would be obtained using a plasma sample. A ratio of concentration value 1 divided by concentration value 2 is determined and is compared to a predetermined ratio of known reliability. If the ratio is less than the predetermined ratio, a false result is present.

The predetermined ratio is a ratio of a concentration of the analyte in a hemolyzed portion of a whole blood sample that contains the analyte divided by a concentration of analyte in plasma, which is the whole blood sample that is treated to remove red blood cells, wherein the concentrations are determined by a method (arbitrarily referred to herein as an "alternate method") other than the method involved in the assay discussed above. The concentrations of analyte used to determine a predetermined ratio of known reliability are measured by a method (alternate method) that is independent of factors that might produce a false result in the assay to which the present embodiments are directed. For example, as discussed above, in assays that involve specific binding reagents such as, for example, immunoassays, the analyte must be determined in a sample that also may contain metabolites of the analyte as well as other binding substances that may bind to the specific binding reagents. This is particularly true in instances where the sample is not subjected to extraction techniques to separate the analyte from other substances such as metabolites and other interfering materials. In such a case, the assay result may not be accurate because the detectable amount of specific binding of the assay reagents to the analyte is affected by the binding of these reagents to other substances, thus producing a false result. In the case of specific binding assays, the method employed to determine analyte concentration in samples and, thus, the predetermined ratio, is one that does not include specific binding reagents. For example, the method may involve liquid chromatography such as, for example, HPLC, either alone or in conjunction with another method that assists in identifying the compounds isolated by the chromatography method such as mass spectroscopy (MS). HPLC with tandem MS is illustrative of such a method.

Thus, in determining a predetermined ratio of known reliability, the alternate method is employed to determine a concentration of the analyte in a hemolyzed portion of a whole blood sample that contains the analyte and a concentration of analyte in a plasma portion of the whole blood sample. Because the alternate method accurately measures analyte concentration regardless of other substances that may be present in the blood sample, the results obtained are considered reliable. The ratio of the concentration of the analyte in a hemolyzed portion of the whole blood sample divided by the concentration of the analyte in the plasma portion of the whole blood sample, both of which are determined by the alternate method, is then considered to be reliable and, therefore, a ratio of known reliability.

The concentrations of the analyte in the blood samples analyzed by the alternate method are selected in view of the therapeutic ranges in patient's samples and drug concentrations that could possibly be found in situations where patients miss their doses or abnormal accumulation of drug due to slow metabolism and clearance or other health factors. The concentrations are similar to those employed in multiple calibration solutions or calibrators, which are a series of samples that contain a known predetermined concentration of analyte that spans the suspected concentration range of interest of the analyte. The calibration or standard solutions may be assayed one or more times and the mean resulting reaction signals are plotted versus their respective known analyte concentrations. The predetermined ratio of known reliability is selected by analyzing the ratios obtained using the alternate method and selecting a ratio that is lower than the lowest of the ratios determined using the alternate method. The lower the ratio selected as the predetermined ratio, the higher is the probability that a false result is accurately determined in the present embodiments.

The data employed to determine the predetermined ratio of known reliability may be taken from known studies. For example, studies have been carried out for the immunosuppressant drug tacrolimus. See, for example, Clin. Chem. 39/6 1045-1049 (1993), which reports that >90% of tacrolimus is bound to erythrocytes in whole blood. The drug distribution ratio (hemolyzed blood/plasma) for tacrolimus obtained from the above study is in the range of about 10 to about 40 where the lower the drug concentration, the lower is the ratio. Furthermore, there may be some health conditions that would lead to a lower drug concentration such as, for example, liver transplant patients might have lower ratio (Ther. Drug Monit., vol 17, No. 2., 1995), for example.

With the existing data from the known studies in mind, a predetermined ratio of known reliability is selected. The value of the predetermined ratio is selected so that a ratio obtained in an immunoassay, for example, assists in the ability to accurately detect and flag false results. In the above example, a predetermined ratio of 3 may be selected and any ratio determined in methods in accordance with the present embodiments that is below 3 is indicative of a false result and should be flagged and discarded. Selecting a predetermined ratio that is less than 100% of the ratio from the known method provides a degree of assurance in the correct detection of false results. In some embodiments the predetermined ratio is less than about 95%, or less than about 90%, or less than about 85%, or less than about 80%, or less than about 75%, or less than about 70%, or less than about 65%, or less than about 60%, or less than about 55%, or less than about 50%, or less than about 45%, or less than about 40%, or less than about 35%, or less than about 30%, or less than about 25%, or less than about 20%, of the known ratio. The lower the above percentage, the higher the confidence level in the prediction of a false result. In an example, by way of illustration and not limitation, selecting a factor of 3 should be useful to flag potential falsely elevated results. In embodiments of assays employing specific binding reagents where non-specific binding is present, essentially all false signal comes from the plasma portion. In such an instance, the ratio is normally close to 1, which, as may be seen, is considerably below the predetermined ratio of 3 for tacrolimus.

Hematocrit is the packed cell volume or erythrocyte volume fraction and is the proportion of blood volume that is occupied by red blood cells. Hematocrit varies from individual to individual is normally about 35 to about 51 for men and 34 to about 47 for women. The hematocrit for an individual blood sample may be determined in a number of different ways including manual and automated methods. Such determinations are well known in the art and will not be repeated here.

The hematocrit factor in accordance with the present embodiments is that number which accounts for the hematocrit of a particular whole blood sample. Because a proportion of whole blood volume is occupied by red blood cells or erythrocytes, the concentration of analyte determined in certain volume of a non-hemolyzed sample, i.e., whole blood, will be less than the concentration of analyte in the same volume of hemolyzed sample because the whole blood has red blood cells that are reducing the effective volume of the non-hemolyzed sample. The hematocrit factor adjusts for the volume of red blood cells in the whole blood. The hematocrit factor for a particular whole blood sample is determined by dividing 1 by 1 minus the hematocrit percentage in decimal form, i.e., by the following equation: 1/(1−hematocrit % in decimal form). For example, if a whole blood sample has a hematocrit of 35% (or 0.35 in decimal form), the hematocrit factor is 1/(1−0.35), which is equal to 1.54. The hematocrit factor is in the range of about 1.4 to about 3.0, or about 1.4 to about 2.5, or about 1.4 to about 2.2, or about 1.5 to about 2.5, or about 1.5 to about 2.2 or about 1.6 to about 2.5, or about 1.6 to about 2.2, for example.

Detailed Discussion of Assays

In many of the assays discussed herein for determination of an erythrocytophilic drug, a label is employed; the label is usually part of a signal producing system ("sps"). The nature of the label is dependent on the particular assay format. An sps usually includes one or more components, at least one component being a detectable label, which generates a detectable signal that relates to the amount of bound and/or unbound label, i.e. the amount of label bound or not bound to the erythrocytophilic drug being detected or to an agent that reflects the amount of the erythrocytophilic drug to be detected. The label is any molecule that produces or can be induced to produce a signal, and may be, for example, a fluorescer, radiolabel, enzyme, chemiluminescer or photosensitizer. Thus, the signal is detected and/or measured by detecting enzyme activity, luminescence, light absorbance or radioactivity, and so forth, as the case may be.

Suitable labels include, by way of illustration and not limitation, enzymes such as alkaline phosphatase, glucose-6-phosphate dehydrogenase ("G6PDH") and horseradish peroxidase; ribozyme; a substrate for a replicase such as QB replicase; promoters; dyes; fluorescers, such as fluorescein, isothiocyanate, rhodamine compounds, phycoerythrin, phycocyanin, allophycocyanin, o-phthaldehyde, and fluorescamine; complexes such as those prepared from CdSe and ZnS present in semiconductor nanocrystals known as Quantum dots; chemiluminescers such as isoluminol; sensitizers; coenzymes; enzyme substrates; radiolabels such as $^{125}I$, $^{131}I$, $^{14}C$, $^3H$, $^{57}Co$ and $^{75}Se$; particles such as latex particles, carbon particles, metal particles including magnetic particles, e.g., chromium dioxide ($CrO_2$) particles, and the like; metal sol; crystallite; liposomes; cells, etc., which may be further labeled with a dye, catalyst or other detectable group. Suitable enzymes and coenzymes are disclosed in Litman, et al., U.S. Pat. No. 4,275,149, columns 19-28, and Boguslaski, et al., U.S. Pat. No. 4,318,980, columns 10-14; suitable fluorescers and chemiluminescers are disclosed in Litman, et al., U.S. Pat. No. 4,275,149, at columns 30 and 31; which are incorporated herein by reference.

The label can directly produce a signal and, therefore, additional components are not required to produce a signal. Numerous organic molecules, for example fluorescers, are able to absorb ultraviolet and visible light, where the light absorption transfers energy to these molecules and elevates them to an excited energy state. This absorbed energy is then dissipated by emission of light at a second wavelength. Other labels that directly produce a signal include radioactive isotopes and dyes.

Alternately, the label may need other components to produce a signal, and the signal producing system would then include all the components required to produce a measurable signal. Such other components may include substrates, coenzymes, enhancers, additional enzymes, substances that react with enzymic products, catalysts, activators, cofactors, inhibitors, scavengers, metal ions, and a specific binding substance required for binding of signal generating substances. A detailed discussion of suitable signal producing systems can be found in Ullman, et al., U.S. Pat. No. 5,185,243, columns 11-13, incorporated herein by reference.

The label or other sps members can be bound to a support. An erythrocytophilic drug derivative or analog may be bound to a solid support in any manner known in the art, provided only that the binding does not substantially interfere with the analogs ability to bind with an antibody. In some embodiments, the erythrocytophilic drug derivative or analog may be coated or covalently bound directly to the solid phase or may have layers of one or more carrier molecules such as poly (amino acids) including proteins such as serum albumins or immunoglobulins, or polysaccharides (carbohydrates) such as, for example, dextran or dextran derivatives. Linking groups may also be used to covalently couple the solid support and the erythrocytophilic drug. Other methods of binding the erythrocytophilic drug derivatives are also possible. For instance, a solid support may have a coating of a binder for a small molecule such as, for example, avidin, an antibody, etc., and a small molecule such as, e.g., biotin, hapten, etc., can be bound to the erythrocytophilic drug derivative or vice versa. The binding of components to the surface of a support may be direct or indirect, covalent or non-covalent and can be accomplished by well-known techniques, commonly available in the literature. See, for example, "Immobilized Enzymes," Ichiro Chibata, Halsted Press, New York (1978) and Cautrecasas, J. Biol. Chem., 245:3059 (1970).

The support may be comprised of an organic or inorganic, solid or fluid, water insoluble material, which may be transparent or partially transparent. The support can have any of a number of shapes, such as particle, including bead, film, membrane, tube, well, strip, rod, planar surfaces such as, e.g., plate, paper, etc., fiber, and the like. Depending on the type of assay, the support may or may not be suspendable in the medium in which it is employed. Examples of suspendable supports are polymeric materials such as latex, lipid bilayers or liposomes, oil droplets, cells and hydrogels, magnetic particles, and the like. Other support compositions include polymers, such as nitrocellulose, cellulose acetate, poly(vinyl chloride), polyacrylamide, polyacrylate, polyethylene, polypropylene, poly(4-methylbutene), polystyrene, polymethacrylate, poly(ethylene terephthalate), nylon, poly(vinyl butyrate), etc.; either used by themselves or in conjunction with other materials.

The support may be a particle. The particles should have an average diameter of at least about 0.02 microns and not more than about 100 microns. In some embodiments, the particles have an average diameter from about 0.05 microns to about 20 microns, or from about 0.3 microns to about 10 microns.

The particle may be organic or inorganic, swellable or non-swellable, porous or non-porous, preferably of a density approximating water, generally from about 0.7 g/mL to about 1.5 g/mL, and composed of material that can be transparent, partially transparent, or opaque. The particles can be biological materials such as cells and microorganisms, e.g., erythrocytes, leukocytes, lymphocytes, hybridomas, streptococcus, *Staphylococcus aureus, E. coli,* viruses, and the like. The particles can also be particles comprised of organic and inorganic polymers, liposomes, latex particles, magnetic or non-magnetic particles, phospholipid vesicles, chylomicrons, lipoproteins, and the like. In some embodiments, the particles are chromium dioxide (chrome) particles or latex particles.

The polymer particles can be formed of addition or condensation polymers. The particles will be readily dispersible in an aqueous medium and can be adsorptive or functionalizable so as to permit conjugation to an erythrocytophilic drug analog, either directly or indirectly through a linking group. The particles can also be derived from naturally occurring materials, naturally occurring materials that are synthetically modified, and synthetic materials. Among organic polymers of particular interest are polysaccharides, particularly cross-linked polysaccharides, such a agarose, which is available as Sepharose, dextran, available as Sephadex and Sephacryl, cellulose, starch, and the like; addition polymers, such as polystyrene, polyvinyl alcohol, homopolymers and copolymers of derivatives of acrylate and methacrylate, particularly esters and amides having free hydroxyl functionalities, and the like.

The label and/or other sps member may be bound to an sbp member or another molecule. For example, the label can be bound covalently to an sbp member such as, for example, an antibody, a receptor for an antibody, a receptor that is capable of binding to a small molecule conjugated to an antibody, or a ligand analog. Bonding of the label to the sbp member may be accomplished by chemical reactions that result in replacing a hydrogen atom of the label with a bond to the sbp member or may include a linking group between the label and the sbp member. Other sps members may also be bound covalently to sbp members. For example, two sps members such as a fluorescer and quencher can each be bound to a different antibody that forms a specific complex with the analyte. Formation of the complex brings the fluorescer and quencher in close proximity, thus permitting the quencher to interact with the fluorescer to produce a signal. Methods of conjugation are well known in the art. See, for example, Rubenstein, et al., U.S. Pat. No. 3,817,837, incorporated herein by reference.

Enzymes of particular interest as label proteins are redox enzymes, particularly dehydrogenases such as glucose-6-phosphate dehydrogenase, lactate dehydrogenase, etc., and enzymes that involve the production of hydrogen peroxide and the use of the hydrogen peroxide to oxidize a dye precursor to a dye. Particular combinations include saccharide oxidases, e.g., glucose and galactose oxidase, or heterocyclic oxidases, such as uricase and xanthine oxidase, coupled with an enzyme which employs the hydrogen peroxide to oxidize a dye precursor, that is, a peroxidase such as horse radish peroxidase, lactoperoxidase, or microperoxidase. Additional enzyme combinations are known in the art. When a single enzyme is used as a label, other enzymes may find use such as hydrolases, transferases, and oxidoreductases, preferably hydrolases such as alkaline phosphatase and beta-galactosidase. Alternatively, luciferases may be used such as firefly luciferase and bacterial luciferase.

Illustrative co-enzymes that find use include NAD[H], NADP[H], pyridoxal phosphate, FAD[H], FMN[H], etc., usually coenzymes involving cycling reactions. See, for example, U.S. Pat. No. 4,318,980, the disclosure of which is incorporated herein by reference.

With label proteins such as, for example, enzymes, the molecular weight range will be from about 10,000 to about 600,000, or from about 10,000 to about 300,000 molecular weight. There is usually at least about 1 erythrocytophilic drug analog per about 200,000 molecular weight, or at least about 1 per about 150,000 molecular weight, or at least about 1 per about 100,000 molecular weight, or at least about 1 per about 50,000 molecular weight, for example. In the case of enzymes, the number of erythrocytophilic drug analog groups is from 1 to about 20, about 2 to about 15, about 3 to about 12, or about 6 to about 10, for example.

The term "non-poly(amino acid) labels" includes those labels that are not proteins (e.g., enzymes). The non-poly (amino acid) label is capable of being detected directly or is detectable through a specific binding reaction that produces a detectable signal. The non-poly(amino acid) labels include, for example, radioisotopes, luminescent compounds, supports, e.g., particles, plates, beads, etc., polynucleotides, and the like. More particularly, the non-poly(amino acid) label can be isotopic or non-isotopic, usually non-isotopic, and can be a polynucleotide coding for a catalyst, promoter, dye, coenzyme, enzyme substrate, radioactive group, a small organic molecule (including, e.g., biotin, fluorescent molecules, chemiluminescent molecules, and the like), amplifiable polynucleotide sequence, a support such as, for example, a particle such as latex or carbon particle or chromium dioxide (chrome) particle or the like, metal sol, crystallite, liposome, cell, etc., which may or may not be further labeled with a dye, catalyst or other detectable group, and the like.

One general group of immunoassays that may be employed includes immunoassays using a limited concentration of antibody. Another group of immunoassays involves the use of an excess of one or more of the principal reagents such as, for example, an excess of an antibody for the immunosuppressant drug. Another group of immunoassays are separation-free homogeneous assays in which the labeled reagents modulate the label signal upon hydrophobic drug-antibody binding reactions. Another group of assays includes labeled antibody reagent limited competitive assays for hydrophobic drug that avoid the use of problematic labeled haptens. In this type of assay, the solid phase immobilized hydrophobic drug analyte is present in a constant, limited amount. The partition of a label between the immobilized hydrophobic drug analyte and free hydrophobic drug analyte depends on the concentration of analyte in the sample.

The assays can be performed either without separation (homogeneous) or with separation (heterogeneous) of any of the assay components or products. Homogeneous immunoassays are exemplified by the EMIT® assay (Syva Company, San Jose, Calif.) disclosed in Rubenstein, et al., U.S. Pat. No. 3,817,837, column 3, line 6 to column 6, line 64; immunofluorescence methods such as those disclosed in Ullman, et al., U.S. Pat. No. 3,996,345, column 17, line 59, to column 23, line 25; enzyme channeling immunoassays ("ECIA") such as those disclosed in Maggio, et al., U.S. Pat. No. 4,233,402, column 6, line 25 to column 9, line 63; the fluorescence polarization immunoassay ("FPIA") as disclosed, for example, in, among others, U.S. Pat. No. 5,354,693; and so forth.

Other enzyme immunoassays are the enzyme modulate mediated immunoassay ("EMMIA") discussed by Ngo and Lenhoff, FEBS Lett. (1980) 116:285-288; the substrate labeled fluorescence immunoassay ("SLFIA") disclosed by Oellerich, J. Clin. Chem. Clin. Biochem. (1984) 22:895-904;

the combined enzyme donor immunoassays ("CEDIA") disclosed by Khanna, et al., Clin. Chem. Acta (1989) 185:231-240; homogeneous particle labeled immunoassays such as particle enhanced turbidimetric inhibition immunoassays ("PETINIA"), particle enhanced turbidimetric immunoassay ("PETIA"), etc.; and the like.

Other assays include the sol particle immunoassay ("SPIA"), the disperse dye immunoassay ("DIA"); the metalloimmunoassay ("MIA"); the enzyme membrane immunoassays ("EMIA"); luminoimmunoassays ("LIA"); and so forth. Other types of assays include immunosensor assays involving the monitoring of the changes in the optical, acoustic and electrical properties of an antibody-immobilized surface upon the binding of a hydrophobic drug. Such assays include, for example, optical immunosensor assays, acoustic immunosensor assays, semiconductor immunosensor assays, electrochemical transducer immunosensor assays, potentiometric immunosensor assays, amperometric electrode assays, and the like.

In one embodiment the assay is an induced luminescence immunoassay, which is described in U.S. Pat. No. 5,340,716 (Ullman, et al.) entitled "Assay Method Utilizing Photoactivated Chemiluminescent Label" ("induced luminescence assay"), which disclosure is incorporated herein by reference. In one approach the assay uses a particle incorporating a photosensitizer and a label particle incorporating a chemiluminescent compound. The label particle is conjugated to an sbp member, for example, an antibody for the hydrophobic drug that is capable of binding to the hydrophobic drug analyte to form a complex, or to a second sbp member to form a complex, in relation to the presence of the erythrocytophilic drug analyte. If the erythrocytophilic drug analyte is present, the photosensitizer and the chemiluminescent compound come into close proximity. The photosensitizer generates singlet oxygen and activates the chemiluminescent compound when the two labels are in close proximity. The activated chemiluminescent compound subsequently produces light. The amount of light produced is related to the amount of the complex formed, which in turn is related to the amount of erythrocytophilic drug analyte present.

By way of further illustration, chemiluminescent particles are employed, which comprise the chemiluminescent compound associated therewith such as by incorporation therein or attachment thereto. An sbp member that binds to the erythrocytophilic drug analyte, such as, for example, an antibody for a erythrocytophilic drug, is bound to a polysaccharide coating the particles. A second sbp member that binds to the erythrocytophilic drug analyte is part of a biotin conjugate. Streptavidin is conjugated to a second set of particles having a photosensitizer associated therewith. The binding of the streptavidin to this second set of particles (photosensitizer particles) may or may not involve a polysaccharide on the particles. The chemiluminescent particles are mixed with either the hemolyzed portion of the whole blood sample or the non-hemolyzed portion of the whole blood sample suspected of containing an erythrocytophilic drug analyte and the photosensitizer particles. The reaction medium is incubated to allow the particles to bind to the erythrocytophilic drug analyte by virtue of the binding of the sbp members to the erythrocytophilic drug analyte. Then, the medium is irradiated with light to excite the photosensitizer, which is capable in its excited state of activating oxygen to a singlet state. Because the chemiluminescent compound of one of the sets of particles is now in close proximity to the photosensitizer by virtue of the presence of the erythrocytophilic drug analyte, it is activated by singlet oxygen and emits luminescence. The medium is then examined for the presence and/or the amount of luminescence or light emitted, the presence thereof being related to the presence and/or amount of the erythrocytophilic drug analyte if the assay produces an accurate result.

Another particular example of an assay that may be employed for the determination of a hydrophobic drug analyte is discussed in U.S. Pat. No. 5,616,719 (Davalian, et al.), which describes fluorescent oxygen channeling immunoassays.

In some embodiments multi-analyte immunoassays may be utilized where the erythrocytophilic drug analyte may be the subject of detection along with one or more other analytes such as other drugs and the like. Such multi-analyte systems are described, for example, in Loor, et al., J. Anal. Toxicol. 12: 299 (1988).

The assays discussed above are normally carried out in an aqueous buffered medium at a moderate pH, generally that which provides optimum assay sensitivity. The pH for the assay medium will usually be in the range of about 4 to about 11, more usually in the range of about 5 to about 10, and preferably in the range of about 6.5 to about 9.5. The pH will usually be a compromise between optimum binding of the binding members of any specific binding pairs, the pH optimum for other reagents of the assay such as members of the signal producing system, and so forth.

Various buffers may be used to achieve the desired pH and maintain the pH during the determination. Illustrative buffers include borate, phosphate, carbonate, tris, barbital and the like. The particular buffer employed is not critical, but in an individual assay one or another buffer may be preferred. Various ancillary materials may be employed in the above methods. For example, in addition to buffers the medium may comprise stabilizers for the medium and for the reagents employed. Frequently, in addition to these additives, proteins may be included, such as albumins; quaternary ammonium salts; polyanions such as dextran sulfate; binding enhancers, or the like.

One or more incubation periods may be applied to the medium at one or more intervals including any intervals between additions of various reagents mentioned above. The medium is usually incubated at a temperature and for a time sufficient for binding of various components of the reagents to occur. Moderate temperatures are normally employed for carrying out the method and usually constant temperature, preferably, room temperature, during the period of the measurement. Incubation temperatures normally range from about 5° to about 99° C., usually from about 15° C. to about 70° C., more usually 20° C. to about 45° C., for example. The time period for the incubation is about 0.2 seconds to about 24 hours, or about 1 second to about 6 hours, or about 2 seconds to about 1 hour, or about 1 to about 15 minutes, for example. The time period depends on the temperature of the medium and the rate of binding of the various reagents, which is determined by the association rate constant, the concentration, the binding constant and dissociation rate constant. Temperatures during measurements will generally range from about 10 to about 50° C., or from about 15 to about 40° C.

The concentration of analyte that may be assayed generally varies from about $10^{-5}$ to about $10^{-17}$ M, more usually from about $10^{-6}$ to about $10^{-14}$ M. Considerations, such as whether the assay is qualitative, semi-quantitative or quantitative (relative to the amount of erythrocytophilic drug analyte present in the sample), the particular detection technique and the concentration of the analyte normally determine the concentrations of the various reagents.

The concentrations of the various reagents in the assay medium will generally be determined by the concentration range of interest of the erythrocytophilic drug analyte, the nature of the assay, and the like. However, the final concentration of each of the reagents is normally determined empirically to optimize the sensitivity of the assay over the range. That is, a variation in concentration of erythrocytophilic drug analyte that is of significance should provide an accurately measurable signal difference. Considerations such as the nature of the signal producing system and the nature of the analytes normally determine the concentrations of the various reagents.

While the order of addition may be varied widely, there will be certain preferences depending on the nature of the assay. The simplest order of addition is to add all the materials simultaneously and determine the effect that the assay medium has on the signal as in a homogeneous assay. Alternatively, the reagents can be combined sequentially. Optionally, an incubation step may be involved subsequent to each addition as discussed above.

Specific Embodiments of Assays

Specific embodiments of assays that may be employed to determine the concentration of analyte in hemolyzed and non-hemolyzed portions of the whole blood sample are discussed next by way of illustration and not limitation.

In a homogeneous assay, after all of the reagents have been combined, the signal is determined and related to the amount of analyte in the sample. For example, in an EMIT® assay for a erythrocytophilic drug, a sample suspected of containing the erythrocytophilic drug is combined in an aqueous medium either simultaneously or sequentially with an enzyme conjugate of the erythrocytophilic drug, i.e., an analog for the erythrocytophilic drug, and antibody capable of recognizing the erythrocytophilic drug. Generally, a substrate for the enzyme is added, which results in the formation of a chromogenic or fluorogenic product upon enzyme catalyzed reaction. Preferred enzymes are glucose-6-phosphate dehydrogenase and alkaline phosphatase but other enzymes may be employed. The erythrocytophilic drug analyte and the moieties of the enzyme conjugate compete for binding sites on the antibody. The enzyme activity in the medium is then determined, usually by spectrophotometric means, and is compared to the enzyme activity determined when calibrators or reference samples are tested in which a known amount of the erythrocytophilic drug is present. Typically, the calibrators are tested in a manner similar to the testing of the sample suspected of containing the erythrocytophilic drug analytes. The calibrators typically contain differing, but known, concentrations of the erythrocytophilic drug analyte to be determined. Preferably, the concentration ranges present in the calibrators span the range of suspected erythrocytophilic drug analyte concentrations in unknown samples.

The aforementioned assays may be carried out using mutant glucose-6-phosphate dehydrogenase as the enzyme of the enzyme conjugate. This mutant enzyme is described in U.S. Pat. Nos. 6,090,567 and 6,033,890, the relevant disclosures of which are incorporated herein by reference. Furthermore, the assay may be conducted using antibodies for the erythrocytophilic drug and using procedures as disclosed in U.S. Pat. Nos. 5,328,828 and 5,135,863, the relevant disclosures of which are incorporated herein by reference.

Heterogeneous assays usually involve one or more separation steps and can be competitive or non-competitive. A variety of competitive and non-competitive assay formats are disclosed in Davalian, et al., U.S. Pat. No. 5,089,390, column 14, line 25 to column 15, line 9, which disclosure is incorporated herein by reference. In one type of competitive assay, a support, as discussed herein, having antibodies for the erythrocytophilic drug bound thereto is contacted with a medium containing the sample and appropriate enzyme conjugates of the erythrocytophilic drug. After separating the support and the medium, the enzyme activity of the support or the medium is determined by conventional techniques and related to the presence and/or amount of the erythrocytophilic drug in the sample.

In certain embodiments a second enzyme may be employed in addition to the enzyme of the enzyme conjugate. The enzymes of the pair of enzymes are related in that a product of the first enzyme serves as a substrate for the second enzyme.

Another embodiment of an assay format is a capture assay. In this assay format, the antibody for the erythrocytophilic drug is covalently bound to a magnetic particle. The sample is incubated with these particles to allow the erythrocytophilic drug in the sample to bind to the antibodies for the erythrocytophilic drug. Subsequently, an enzyme that has the erythrocytophilic drug or a derivative of the erythrocytophilic drug covalently attached is incubated with the magnetic particles. After washing, the amount of enzyme that is bound to the magnetic particles is measured and is inversely related to the presence and/or amount of the erythrocytophilic drug in the sample.

The following specific assay descriptions are by way of illustration of, and not as a limitation on, the scope of the present invention. Selection of sirolimus as the erythrocytophilic drug is also by way of illustration and not limitation as the present invention has general application to detection of erythrocytophilic drugs in general and immunosuppressant drugs in particular.

In one embodiment, the test sample or a sirolimus standard is mixed with a sirolimus conjugate, i.e., for example, an analog of sirolimus that is attached to biotin. The sirolimus of the test sample and the analog of sirolimus are allowed to compete for binding to the antibody for the sirolimus, which is capable of binding to sirolimus or the analog of sirolimus. After rinsing with an appropriate wash buffer, a detection molecule consisting of streptavidin or avidin conjugated to an enzyme, florescent or chemiluminescent molecule or radioactive moiety can be added to the medium, which is then examined for the presence and/or amount of signal. The presence and/or amount of signal are related to the presence and/or amount of sirolimus.

In one embodiment the assay employed is an induced luminescence assay as described above. The reagents include two latex bead reagents and a biotinylated anti-sirolimus mouse monoclonal antibody. The first bead reagent is coated with sirolimus or a sirolimus analog and contains chemiluminescent dye. The second bead reagent is coated with streptavidin and contains a photosensitizer dye. In a first step, sample suspected of containing sirolimus is incubated with biotinylated antibody for sirolimus, which allows sirolimus from the sample to saturate a fraction of the biotinylated antibody that is directly related to the sirolimus concentration. In a second step, the first bead reagent is added and leads to the formation of bead/biotinylated antibody immunocomplexes with the non-saturated fraction of the biotinylated antibody. The second bead reagent is then added and binds to the biotin to form bead pair immunocomplexes. When illuminated by light at 680 nm, the second bead reagent converts dissolved oxygen in the reaction solution into the more energetic singlet oxygen form. In the bead pairs, the singlet oxygen diffuses into the first bead reagent thereby triggering a chemiluminescent reaction. The resulting chemiluminescent signal is measured at 612 nm and is an inverse function of the concentration of sirolimus in the sample. The amount of this signal is related to the presence and or amount of sirolimus in the sample.

A specific example of another assay format is ACMIA (Affinity Chromium dioxide Mediated Immuno Assay). For the ACMIA assay format, chrome particles, which are coated with sirolimus or a sirolimus analog, are employed as a first component. A second component is an antibody for sirolimus. This antibody, crosslinked to a reporter enzyme (for example, beta-galactosidase), is added to a reaction vessel in an excess amount, i.e., an amount greater than that required to bind all of the analyte that might be present in a sample. The antibody-enzyme conjugate is mixed with a sample suspected of containing sirolimus to allow the sirolimus analyte to bind to the antibody. Next, the chrome particle reagent is added to bind up any excess antibody-enzyme conjugate. Then, a magnet is applied, which pulls all of the chrome particles and excess antibody-enzyme out of the suspension, and the supernatant is transferred to a final reaction container. The substrate of the reporter enzyme is added to the final reaction container, and the enzyme activity is measured spectrophotometrically as a change in absorbance over time. The amount of this signal is related to the presence and/or amount of sirolimus in the sample.

In a sandwich assay format, a first reagent comprising chrome particles coated with anti-sirolimus antibodies and a second reagent comprising a second antibody (or binding protein) for the first antibody conjugated to a reporter enzyme are employed. In this format, the sample suspected of containing sirolimus is incubated with the chrome particles so that all of the sirolimus, if present in the sample, becomes bound to the chrome particles. The chrome particles are washed, using a magnet to separate the bound analyte from the supernatant. Then, the second reagent, i.e., antibody (or binding protein) conjugated to a reporter enzyme, is incubated with the chrome particles to form a "sandwich". After washing, the amount of enzyme that is bound to the chrome is measured and is related to the presence and/or amount of sirolimus in the sample.

Another assay format is EMIT® (Enzyme-Mediated Immunoassay Technology). In this assay format, an enzyme conjugate is formed such as, for example, a conjugate of G-6-PDH and a sirolimus analog. An antibody for sirolimus is incubated with the enzyme-conjugate and a sample suspected of containing sirolimus. Antibody for sirolimus binds to the sirolimus analyte in the sample instead of binding to the enzyme conjugate, which reduces the amount of inhibition of the enzyme activity that might otherwise occur in the absence of sirolimus in the sample. In this way, samples with more sirolimus analyte will yield higher enzyme activity, and samples with no sirolimus analyte will have the maximum inhibition and the lowest enzyme activity. The amount of reduction of inhibition of enzyme activity is related to the amount of sirolimus in the sample.

Kits for Conducting Assays on the Sample Portions

The reagents for conducting a particular assay on a hemolyzed or non-hemolyzed sample portion may be present in a kit useful for conveniently performing an assay for the determination of an erythrocytophilic drug analyte. In one embodiment a kit comprises in packaged combination an antibody for an erythrocytophilic drug analyte and other reagents for performing an assay, the nature of which depend upon the particular assay format. The reagents may each be in separate containers or various reagents can be combined in one or more containers depending on the cross-reactivity and stability of the reagents. The kit can further include other separately packaged reagents for conducting an assay such as additional sbp members, ancillary reagents such as an ancillary enzyme substrate, and so forth.

The relative amounts of the various reagents in the kits can be varied widely to provide for concentrations of the reagents that substantially optimize the reactions that need to occur during the present method and further to optimize substantially the sensitivity of the assay. Under appropriate circumstances one or more of the reagents in the kit can be provided as a dry powder, usually lyophilized, including excipients, which on dissolution will provide for a reagent solution having the appropriate concentrations for performing a method or assay in accordance with the present invention. The kit can further include a written description of a method in accordance with the present embodiments as described above.

The following examples further describe the specific embodiments of the invention by way of illustration and not limitation and are intended to describe and not to limit the scope of the invention. Parts and percentages disclosed herein are by volume unless otherwise indicated.

EXAMPLES

All chemicals may be purchased from the Sigma-Aldrich Company (St. Louis Mo.) unless otherwise noted. Tacrolimus may be obtained from Wyeth Pharmaceuticals, Madison N.J.

Testing is carried out using the DIMENSION® RxL analyzer, available from Dade Behring Inc., Newark Del. The instrument is employed using ACMIA immunoassay technology. The ACMIA assay method is disclosed in U.S. Pat. Nos. 7,186,518, 5,147,529, 5,128,103, 5,158,871, 4,661,408, 5,151,348, 5,302,532, 5,422,284, 5,447,870, 5,434,051, the disclosures of which are incorporated herein in their entirety. In the embodiment of the ACMIA method used herein and discussed in more detail below, competition between tacrolimus analog on chrome particles and tacrolimus in patient samples for antibody for tacrolimus conjugated to an enzyme (conjugate) is utilized to determine the amount of tacrolimus in the patient samples. Conjugate that binds to the tacrolimus analog on chrome particles is removed by magnetic separation. The enzymatic activity from conjugate remaining in the supernatant is measured and is directly proportional to the amount of tacrolimus in the patient sample. In the ACMIA assay format employed, the enzymatic activity observed when testing a sample containing no tacrolimus is indicative of the amount of enzymatic activity that is not bound to active antibody (i.e., cannot bind tacrolimus on chrome particles). The enzymatic activity observed when no chrome particle is present is indicative of the total amount of enzymatic activity in the conjugate. These values can be used to estimate the percent of enzymatic activity bound to active antibody.

Example 1

Automated Immunoassay for Tacrolimus Detection of False Results

Preparation of hemolytic pretreatment solution. This pretreatment solution is prepared to contain 15 µg/mL of a FK-506 carbamate compound (tacrolimus ester), 6.8 mg/mL PIPES™ 1.5 sodium salt, 0.3 mg/mL EDTA Disodium, 1.0 mg/mL Saponin, 0.2% Proclin 300, 0.024 mg/mL Neomycin sulfate and 0.99 mg/mL $NaN_3$, pH 6.5. The FKE concentration in the final reaction mixture is 3.4 µg/mL. Table 1 shows the composition of the hemolysis reagent for use in hemolyzing a portion of a whole blood sample for assay for Tacrolimus (AI=as indicated).

TABLE 1

| Name | Qty. (per mL) | Function |
|---|---|---|
| FK506 Ester | 15 µg | dissociates Tacrolimus from binding protein |
| SesquiNa PIPES | 6.8 mg | buffer |
| EDTA Disodium | 0.3 mg | preventing clot-formation |
| Saponin | 1.0 mg | blood cell lysis |
| Proclin 300 | 2 µL | preservative |
| Neomycin Sulfate | 0.024 mg | preservative |
| NaN3 | 0.99 mg | preservative, matrix |

Preparation of non-hemolytic pretreatment solution. This solution is the same as the hemolytic pretreatment solution described above with the exception that the solution lacks the hemolytic reagent (Saponin) and contains a salt at a concentration to make the solution isotonic or slightly hypertonic. The salt may be, for example, NaCl, or KCl, or the like. The salt concentration is about 0.85 to 12% (weight to volume). In the pretreatment solution for these examples, the salt concentration is about 2%.

Preparation of anti-tacrolimus antibody-β-galactosidase conjugate. Monoclonal anti-tacrolimus antibody (obtainable from Wyeth Pharmaceuticals, Cambridge Mass.) is conjugated to β-galactosidase using a standard heterobifunctional SMCC (succinimidyl trans-4-(N-maleimidylmethyl)cyclohexane-1-carboxylate) linker according to known techniques. The antibody conjugate solution contains approximately 7.5 µg/mL anti-tacrolimus antibody-β-galactosidase conjugate, 30 mg/mL protease free bovine serum albumin, 0.126 mg/mL $MgCl_2$, 0.03 mL/mL of ethylene glycol, 35.14 mg/mL PIPES 1.5 sodium salt, 50 mg/mL NaCl and beta-gal mutein (inactivated beta-galactosidase), pH 6.5.

Magnetic chrome particle preparation. Tacrolimus chrome particles (immunoassay solid phase) are prepared by conjugating tacrolimus-C26- or —C32-CMO conjugate to DA10-Dexal-Chromium Dioxide particles using N-hydroxysuccinimide (NHS) ester and 1-ethyl-3-(3-dimethylaminopropyl) carbodiimide (EDAC) chemistry. See, for example, U.S. Pat. No. 6,231,982, the relevant disclosure of which is incorporated herein by reference. The tacrolimus chrome particles are then made into tacrolimus chrome particle tablets. Each tacrolimus tablet contains approximately 2 mg tacrolimus chrome particle slurry, 30.4 mg trehalose dihydrate and 3.6 mg CARBOWAX® 100 µm.

Tacrolimus Assay. The principle and operation of the ACMIA assay for tacrolimus for detection of false results is as follows: A whole blood sample (hematocrit 43%) suspected of containing tacrolimus is divided into two equal portions of 18 µL each (Portion A and Portion B). Portion A is combined with a hemolytic pretreatment reagent prepared as described above in a reaction vessel on the DIMENSION® RxL analyzer. The whole blood is sampled from a standard cup by first mixing the blood with the ultrasonic sample probe. The mixing of whole blood sample with the pretreatment solution ensures the hemolysis of the whole blood and the displacement of the protein-bound tacrolimus molecules from their binding sites when the tacrolimus carbamate molecules were present.

Portion B is combined with a non-hemolytic pretreatment reagent prepared as described above in a separate reaction vessel on the DIMENSION® RxL analyzer. The whole blood is sampled from a standard cup by first mixing the blood with the ultrasonic sample probe. The mixing of whole blood sample with the pretreatment solution ensures the displacement of the protein-bound tacrolimus molecules from their binding sites when the tacrolimus carbamate molecules were present.

Anti-tacrolimus antibody-β-galactosidase conjugate (50 µL) is added next to each of the reaction vessels and the mixture is held for a period of time (10 to 15 minutes) and at a temperature of 43° C. to allow tacrolimus, if present, to react with the antibody reagent. Chrome particles with immobilized tacrolimus-CMO-DA10-Dexal are added (50 µL) to each of the reaction vessels and are allowed to bind un-bound conjugate. The tacrolimus-bound anti-tacrolimus antibody-β-galactosidase conjugate does not bind to the chrome particles but remains in the supernatant when a magnetic field is applied to the above reaction mixtures to separate the solution from the chrome particles. The tacrolimus-bound conjugate is detected by transferring the supernatant from each of the reaction vessels to a photometric cuvette and measuring the enzymatic rate of the conjugate in the presence of chlorophenol red-β-D-galactopyranoside (CPRG). The rate for each reaction vessel is measured bichromatically at 577 and 700 nm.

For one whole blood sample tested as described above, the signal obtained for Portion A corresponds to a measured drug concentration in Portion A of 20 ng/mL and the signal obtained for Portion B corresponds to a measured drug concentration in Portion B of 6 ng/mL. In accordance with present embodiments, the concentration in Portion B is multiplied by a hemocrit factor, which in the present example is $1/(1-0.43)$, and the result is 10.5 ng/mL. The ratio is 20 ng/mL÷10.5 ng/mL or 1.9. This ratio is below the predetermined ratio of 3, which is selected from a review of the studies in Clin. Chem. 39/6 1045-1049 (1993) as discussed above. Therefore, this assay result is flagged as a false result.

For another whole blood sample tested as described above, the signal obtained for Portion A corresponds to a drug concentration in Portion A of 20 ng/mL and the signal obtained for Portion B corresponds to a drug concentration in Portion B of 6.6 ng/mL. In accordance with present embodiments, the concentration in Portion B is multiplied by a hemocrit factor, which in the present example is $1/(1-0.43)$, and the result is 11.6 ng/mL. The ratio is 20 ng/mL÷11.6 ng/mL or 1.7. This ratio is below the predetermined ratio of 3, and therefore, this assay result is flagged as a false result.

For another whole blood sample tested as described above, the signal obtained for Portion A corresponds to a drug concentration in Portion A of 20 ng/mL and the signal obtained for Portion B corresponds to a drug concentration in Portion B of 3.5 ng/mL. In accordance with present embodiments, the concentration in Portion B is multiplied by a hemocrit factor, which in the present example is $1/(1-0.43)$, and the result is 6.1 ng/mL. The ratio is 20 ng/mL÷6.1 ng/mL or 3.3. This ratio is above the predetermined ratio of 3, and therefore, this assay result is accepted as an accurate result and is not flagged as a false result.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims. Furthermore, the foregoing description, for purposes of explanation, used specific nomenclature to provide a thorough understanding of the invention. However, it will be apparent to one skilled in the art that the specific details are not required in order to practice the invention.

Thus, the foregoing descriptions of specific embodiments of the present invention are presented for purposes of illustration and description; they are not intended to be exhaustive or to limit the invention to the precise forms disclosed. Many modifications and variations are possible in view of the above teachings. The embodiments were chosen and described in order to explain the principles of the invention and its practical applications and to thereby enable others skilled in the art to utilize the invention.

What is claimed is:

1. A method for detecting a false result in an assay for determining a concentration of an erythrocytophilic analyte in a whole blood sample suspected of containing the erythrocytophilic analyte, the method comprising:
    (a) determining by means of the assay a concentration of the erythrocytophilic analyte utilizing a hemolyzed portion of the blood sample to obtain concentration value 1,
    (b) determining by means of the assay a concentration of the erythrocytophilic analyte utilizing a non-hemolyzed portion of the blood sample and multiplying the concentration times a hematocrit factor to obtain concentration value 2,
    (c) determining a ratio of concentration value 1 divided by concentration value 2, and
    (d) comparing the ratio from (c) to a predetermined ratio of known reliability wherein, if the ratio is less than the predetermined ratio, a false result is indicated.

2. The method of claim 1 wherein the predetermined ratio of known reliability is determined by a method that is independent of factors that produce a false result in the assay and wherein the predetermined ratio is a ratio of a concentration of the erythrocytophilic analyte in a hemolyzed portion of a different whole blood sample that contains the erythrocytophilic analyte divided by a concentration of erythrocytophilic analyte in a non-hemolyzed portion of the different whole blood sample.

3. The method according to claim 1 wherein the hematocrit factor is the following equation: 1/(1−hematocrit % in decimal form).

4. The method according to claim 1 wherein the assay comprises:
    (i) combining the blood sample of step (a) with reagents for determining the concentration of the erythrocytophilic analyte in the blood sample of step (a) wherein the reagents comprise at least one antibody for the erythrocytophilic analyte, and combining the blood sample of step (b) with reagents for determining the concentration of the erythrocytophilic analyte in the blood sample of step (b) wherein the reagents comprises at least one antibody for the erythrocytophilic analyte, and
    (ii) measuring an amount of a complex comprising the erythrocytophilic analyte and the antibody for the erythrocytophilic analyte for the blood sample of step (a) and the blood sample of step (b) and relating the amount of the complex to the concentration of the erythrocytophilic analyte in the blood sample of step (a) and the blood sample of step (b).

5. The method according to claim 4 wherein the reagents in step (i) further comprise an analog of the erythrocytophilic analyte that comprises a label.

6. The method according to claim 4 wherein in step (i) a second antibody is added to the blood sample and reagents in step a) and step b) wherein the second antibody binds to the antibody for the erythrocytophilic analyte in the complex.

7. The method according to claim 6 wherein at least one of either the antibody for the erythrocytophilic analyte or the second antibody comprises a label.

8. The method according to claim 4 wherein one of the reagents comprises a label.

9. The method according to claim 4 wherein one of the reagents comprises a particle.

10. The method according to claim 4 wherein one of the reagents is an erythrocytophilic analyte analog linked to an enzyme label and one of the reagents is an antibody for the erythrocytophilic analyte attached to a magnetic particle.

11. A method for detecting a false result in an assay for determining a concentration of an erythrocytophilic analyte in a whole blood sample suspected of containing the erythrocytophilic analyte, the method comprising:
    (a) determining by means of the assay a concentration of the erythrocytophilic analyte utilizing a hemolyzed portion of the blood sample to obtain concentration value 1,
    (b) determining by means of the assay a concentration of the erythrocytophilic analyte utilizing a non-hemolyzed portion of the blood sample and multiplying the concentration times a hematocrit factor to obtain concentration value 2 wherein the hematocrit factor is the following equation: 1/(1−hematocrit % in decimal form),
wherein the assay comprises:
    (i) combining the blood sample of step (a) with reagents for determining the concentration of the erythrocytophilic analyte in the blood sample of step (a) wherein the reagents comprise at least one antibody for the erythrocytophilic analyte, and combining the blood sample of step (b) with reagents for determining the concentration of the erythrocytophilic analyte in the blood sample of step (b) wherein the reagents comprises at least one antibody for the erythrocytophilic analyte, and
    (ii) measuring an amount of a complex comprising the erythrocytophilic analyte and the antibody for the erythrocytophilic analyte for the blood sample of step (a) and the blood sample of step (b) and relating the amount of the complex to the concentration of the erythrocytophilic analyte in the blood sample of step (a) and the blood sample of step (b),
    (c) determining a ratio of concentration value 1 divided by concentration value 2, and
    (d) comparing the ratio from (c) to a predetermined ratio of known reliability wherein, if the ratio is less than the predetermined ratio, a false result is indicated and wherein the predetermined ratio of known reliability is determined by a method that is independent of factors that produce a false result in the assay and wherein the predetermined ratio is a ratio of a concentration of the erythrocytophilic analyte in a hemolyzed portion of a different whole blood sample that contains the erythrocytophilic analyte divided by a concentration of erythrocytophilic analyte in a non-hemolyzed portion of the different whole blood sample.

12. The method according to claim 11 wherein the erythrocytophilic analyte is selected from the group consisting of tacrolimus, sirolimus and cyclosporin.

13. The method according to claim 11 wherein the erythrocytophilic analyte is an immunosuppressant drug.

14. The method according to claim 11 wherein the assay method is a heterogeneous assay method.

15. The method according to claim 11 wherein the reagents in step (i) further comprise an analog of the erythrocytophilic analyte that comprises a label.

16. The method according to claim 11 wherein in step (i) a second antibody is added to the blood sample and reagents in step a) and step b) wherein the second antibody binds to the antibody for the erythrocytophilic analyte in the complex.

17. The method according to claim 16 wherein at least one of either the antibody for the analyte or the second antibody comprises a label.

18. The method according to claim 11 wherein one of the reagents comprises a label.

19. The method according to claim 11 wherein one of the reagents comprises a particle.

20. The method according to claim 11 wherein one of the reagents is an erythrocytophilic analyte analog linked to an enzyme label and one of the reagents is an antibody for the erythrocytophilic analyte attached to a magnetic particle.

* * * * *